United States Patent
Tharpe, Jr. et al.

(10) Patent No.: US 6,345,660 B2
(45) Date of Patent: *Feb. 12, 2002

(54) LAMINATING APPARATUS HAVING DANCER AND AIR SHAFT AND ASSOCIATED METHODS

(76) Inventors: John M. Tharpe, Jr.; Robert M. Herrin, both of 1005 Willie Pitts Jr. Rd., P.O. Box 3970, Albany, GA (US) 31706

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/089,777

(22) Filed: Jun. 3, 1998

(51) Int. Cl.[7] .......................... B65H 21/00; B32B 31/00
(52) U.S. Cl. ...................... 156/494; 156/157; 156/164; 156/502; 156/504; 242/552; 242/555.4; 242/577
(58) Field of Search ................................ 156/157, 159, 156/502, 504, 164, 494; 242/552, 555, 555.3, 555.4, 571.2, 577

(56) References Cited

U.S. PATENT DOCUMENTS

| | | | | |
|---|---|---|---|---|
| 3,644,157 A | * | 2/1972 | Draper ................... | 156/164 X |
| 4,309,236 A | * | 1/1982 | Teed ......................... | 156/164 |
| 4,704,171 A | * | 11/1987 | Thompson et al. ........... | 156/64 |
| 4,915,282 A | * | 4/1990 | Martin et al. ................ | 226/44 |
| 5,411,223 A | * | 5/1995 | Gatteschi .................... | 242/551 |
| 5,509,618 A | * | 4/1996 | Kleiman et al. ......... | 242/571.2 |
| 5,699,978 A | * | 12/1997 | Hanazawa .................. | 242/552 |
| 5,873,966 A | * | 2/1999 | Goldberg et al. ....... | 156/157 X |

OTHER PUBLICATIONS

Brochure: Series 20 for Elastic Diapers; Paper Converting Machine Company, Green Bay, WI, Oct. 1982.*

* cited by examiner

Primary Examiner—Mark A. Osele
(74) Attorney, Agent, or Firm—Allen, Dyer, Doppelt, Milbrath & Gilchrist, P.A.

(57) ABSTRACT

A laminating apparatus and methods are provided for laminating fabric such as for a disposable garment. The apparatus preferably includes a frame having upper and lower frame regions, a first roll of fabric mounted to the upper frame region so as to provide a first web of fabric when unwound from the first fabric roll, and a second roll of fabric mounted to the lower frame region and positioned adjacent the first fabric roll so as to provide a second web of fabric when unwound from the second fabric roll. A fabric dance controller is preferably positioned downstream from the first and second fabric rolls and positioned to receive the first and second webs of fabric therefrom for dancingly controlling the tension of the first and second webs of fabric being received from the first and second fabric rolls. Additionally, a fabric laminator is preferably positioned downstream from said fabric dance controlling means and positioned to receive the first and second webs of fabric for combiningly laminating the first and second webs of fabric to thereby provide a laminated web of fabric therefrom.

22 Claims, 7 Drawing Sheets

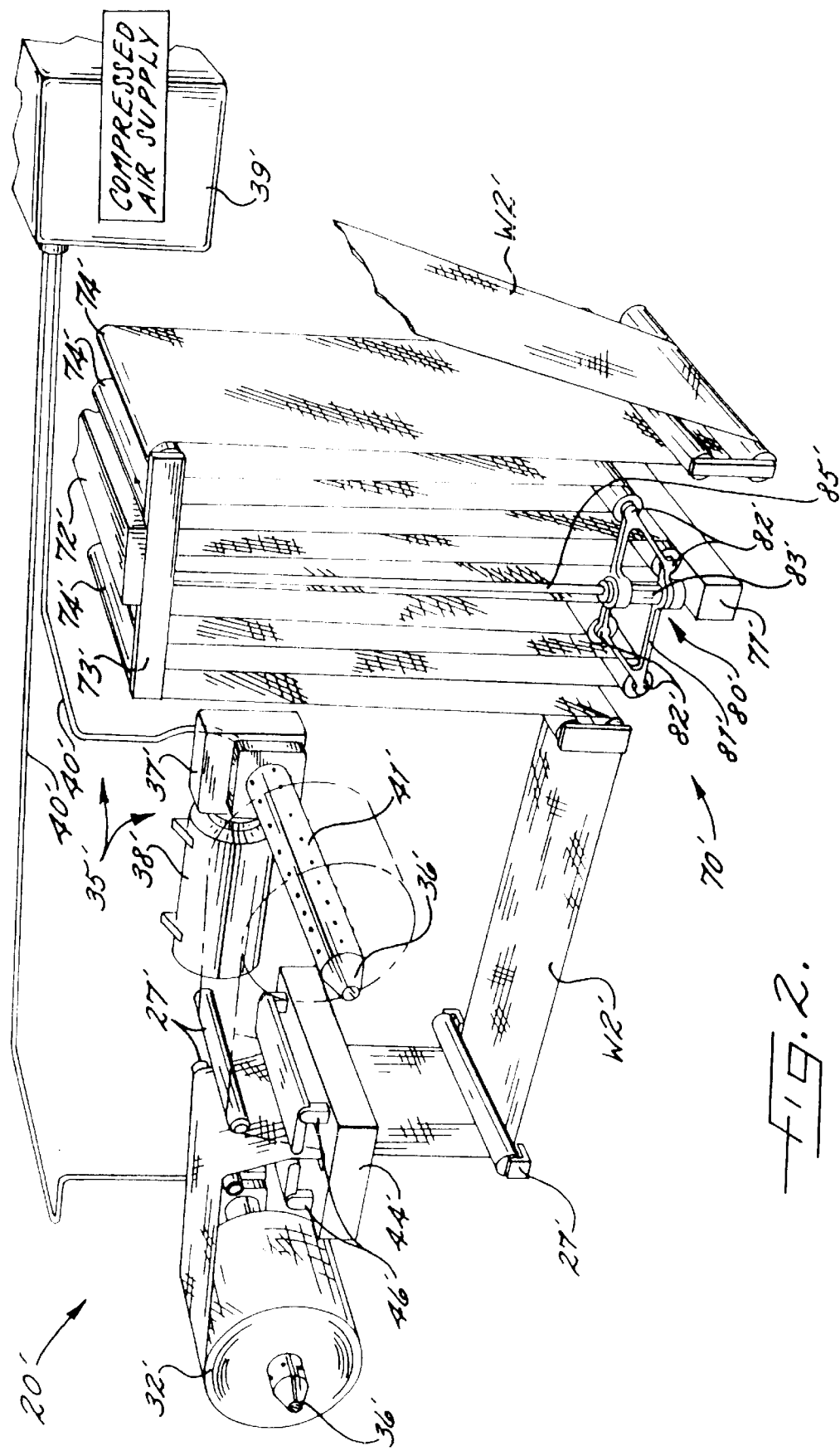

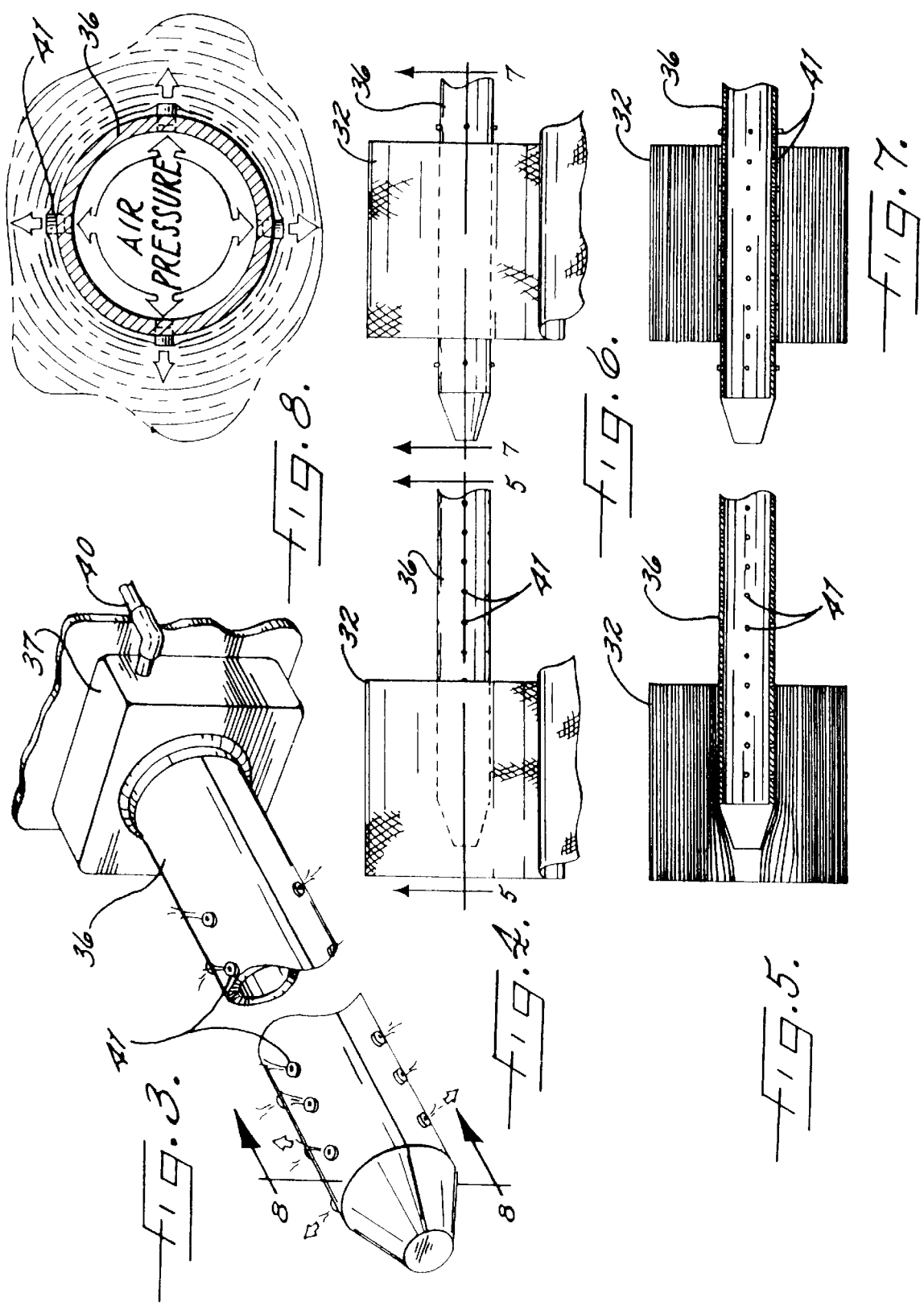

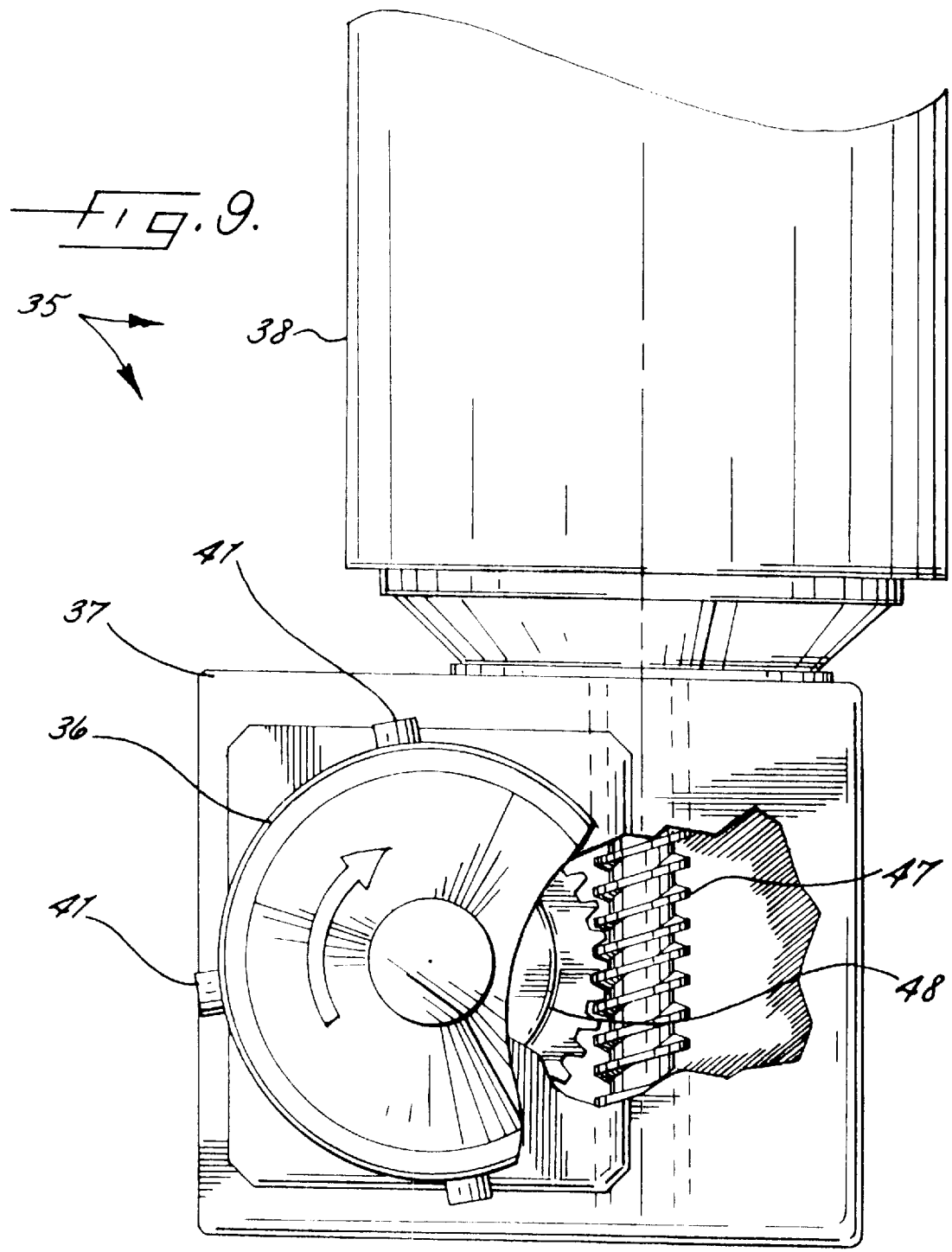

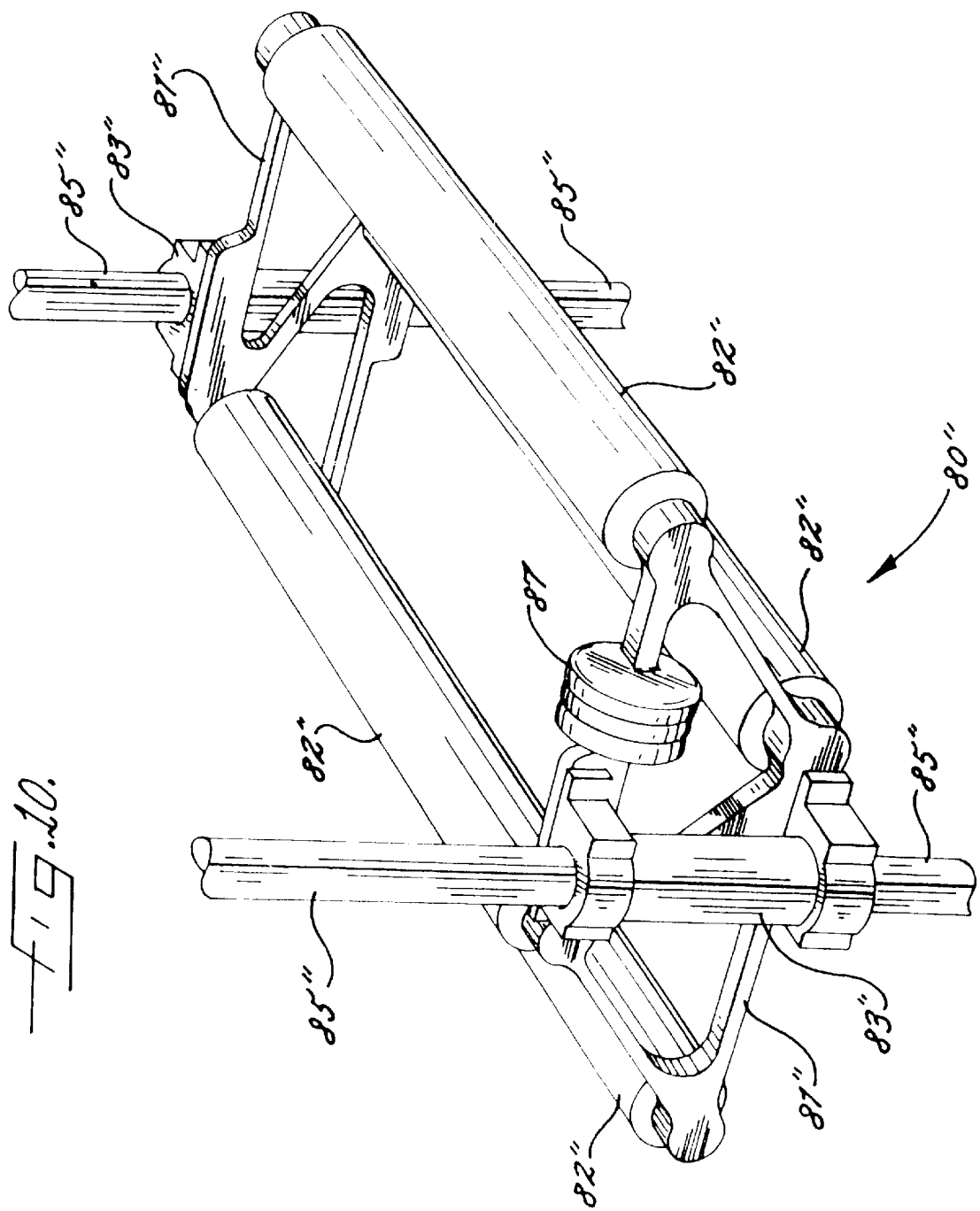

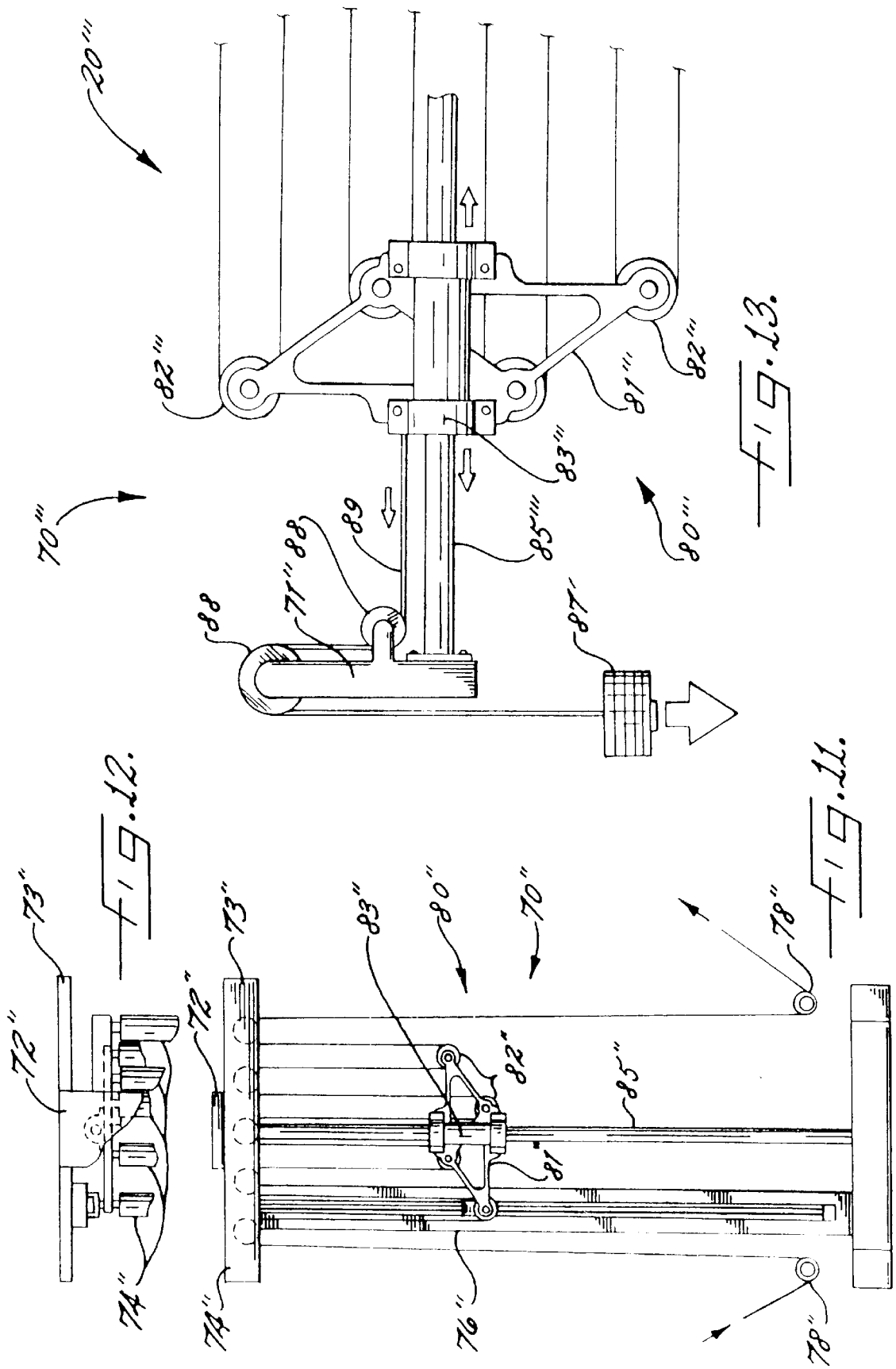

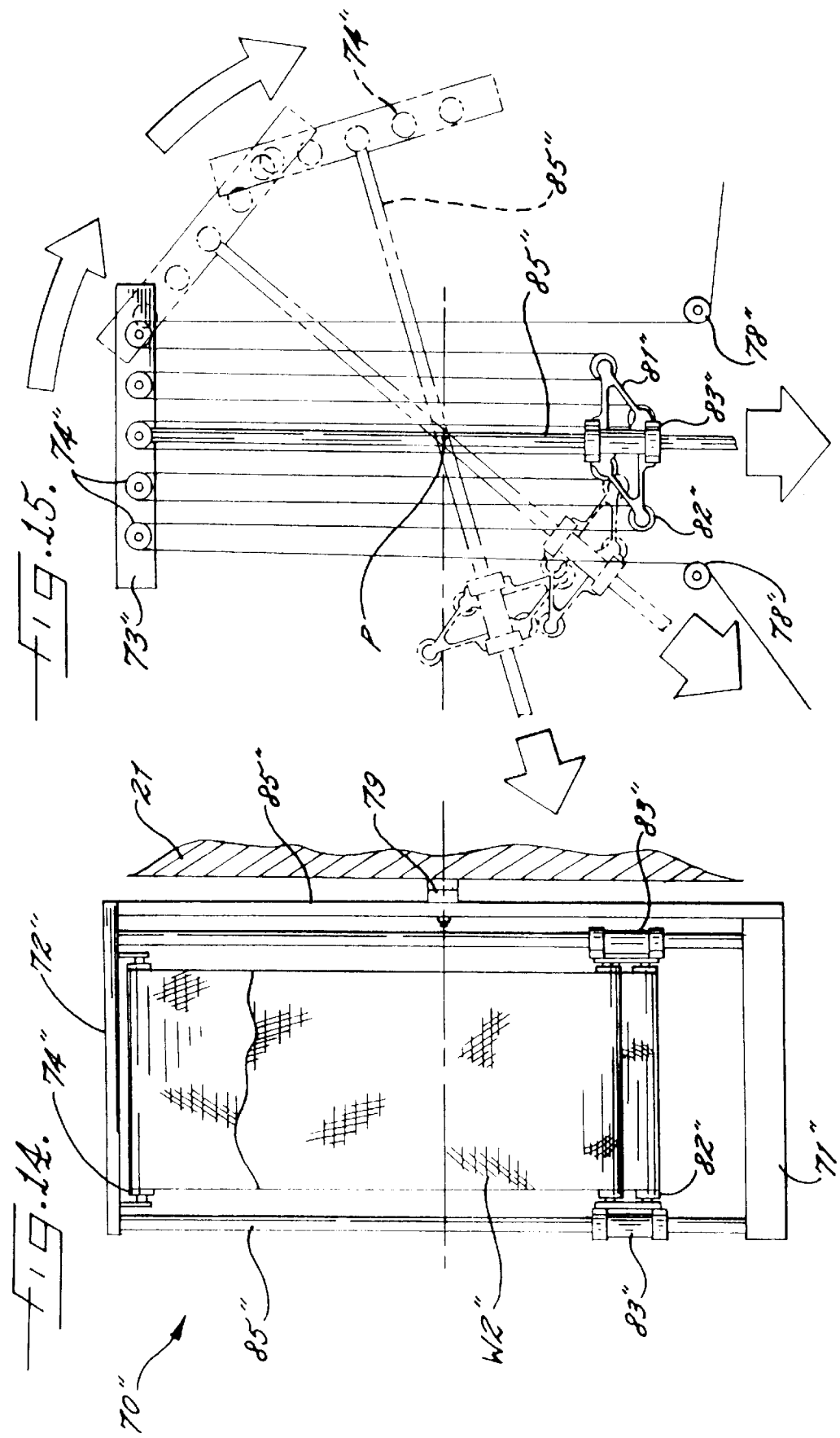

LAMINATING APPARATUS HAVING DANCER AND AIR SHAFT AND ASSOCIATED METHODS

FIELD OF THE INVENTION

The invention relates to the field of disposable products, and, more particularly, to laminating fabric for disposable garments.

BACKGROUND OF THE INVENTION

Fabric or layers of material are often formed, sealed, adhered, or positioned so as to overlie or underlie one another to thereby in combination form a laminate or laminated material. For laminating fabric, these layers often involve two rolls of fabric mounted or positioned to unwind so that the webs of material being unwound are combined in an overlying and/or underlying relationship to form a laminate fabric. These laminators when used in a production line, however, can have problems when one or more of the webs breaks, is damaged, or has problems associated with a smooth and continuous production line.

Additionally, tension control of moving webs of fabric is commonly monitored and controlled by the use of a dancer system. Many types of dancer systems have been developed over the years. A basic form of such a system, for example, includes a web of fabric being transported along a conveying system such as rollers, rolls, or conveyor belts being driven by motors. A dancer roll is preferably positioned in line with the conveying system so that the web passes over or engages the dancer roll. The dancer roll is preferably connected to a distal end of a dancer support arm and extends outwardly therefrom. The proximal end of the dancer support arm is preferably pivotally connected to a fixed position or mount so that the dancer roll "dances" or moves along the pivotal direction of the dancer support arm with the varying tension from the web, e.g., moving at different speeds. This dancer system, however, also has several problems associated therewith. For example, the inertia of the dancer can cause the tension control to generally be non-linear with little dynamic response. In other words, when the dancer is being pulled up by the web of material positioned thereon, additional tension is required to start the dancer moving. This problem can become worse, for example, if the mass of the dancer is increased or the arm lengthens. Also, the dancer system provides little or no flexibility for readily adjusting tension within a system such as when a portion of a manufacturing line has problems or goes down.

SUMMARY OF THE INVENTION

In view of the foregoing background, the present invention advantageously provides an apparatus and methods for laminating fabric which reduce down time associated with damage, breaks, or other problems with one or more of the layers of fabric being laminated. The present invention also advantageously provides a quad-laminator having a dancer for increasing control of and flexibility in adjusting the tension of the webs of fabric being laminated. The present invention also advantageously provides an apparatus for laminating fabric having an air shaft associated therewith for readily mounting, removing, and driving rolls of fabric. The present invention further provides a dancer having increased tension control for moving webs of fabric. The present invention still further provides an air shaft for readily mounting, removing, and driving rolls of fabric.

An apparatus according to the present invention is provided for laminating fabric for a disposable garment according to the present invention. The apparatus preferably includes a frame, a first roll of fabric mounted to the frame so as to provide a first web of fabric when unwound from the first fabric roll, and a second roll of fabric mounted to the frame and positioned adjacent the first fabric roll so as to provide a second web of fabric when unwound from the second fabric roll. A fabric dance controller is preferably positioned downstream from the first and second fabric rolls and positioned to receive the first a and second webs of fabric therefrom for dancingly controlling the tension of the first and second webs of fabric being received from the first and second fabric rolls. Additionally, a fabric laminator is preferably positioned downstream from said fabric dance controlling means and positioned to receive the first and second webs of fabric for combiningly laminating the first and second webs of fabric to thereby provide a laminated web of fabric therefrom.

More particularly, according to other aspects of the present invention, the apparatus advantageously can include a laminating frame having upper and lower laminating frame regions, a first roll of fabric mounted to the upper laminating frame region so as to provide a first web of fabric when unwound from the first fabric roll, and a second roll of fabric mounted to the lower laminating frame region and positioned adjacent the first fabric roll so as to provide a second web of fabric when unwound from said second fabric roll. The apparatus can also include a third redundant roll of fabric mounted to the upper laminating frame region and positioned adjacent the first fabric roll so as to provide a third web of fabric when unwound from the third fabric roll and a fourth redundant roll of fabric mounted to the lower frame region and positioned adjacent the second and third fabric rolls so as to provide a fourth web of fabric when unwound from the fourth fabric roll. A first splicer is preferably mounted to the upper laminating frame region for splicing the third web of fabric to the first web of frame and a second splicer is preferably mounted to the lower laminating frame region for splicing the fourth web of fabric to the second web of fabric. The apparatus preferably further includes fabric dance controlling means mounted to the laminating frame, positioned downstream from at least the first and second fabric rolls, and positioned to receive at least the first and second webs of fabric therefrom for dancingly controlling the tension of at least the first and second webs of fabric being received from at least the first and second fabric rolls and fabric laminating means mounted to the laminating frame, positioned downstream from the fabric dance controlling means, and positioned to receive at least the first and second webs of fabric for combiningly laminating at least the first and second webs of fabric to thereby provide a laminated web of fabric therefrom.

The present invention also advantageously provides methods of laminating fabric for a disposable garment. A method preferably includes mounting a first roll of fabric to a frame so as to provide a first web of fabric when unwound from the first fabric roll, mounting a second roll of fabric to the frame and positioned adjacent the first fabric roll so as to provide a second web of fabric when unwound from the second fabric roll, dancingly controlling the tension of at least one of the first and second webs of fabric being received from at least one of the first and second fabric rolls, and combiningly laminating the first and second webs of fabric to thereby provide a laminated web of fabric therefrom.

Another method of laminating fabric for a disposable garment according to the present invention preferably includes dancingly controlling the tension of at least one of first and second webs of fabric being received from at least one of respective first and second fabric rolls and combiningly laminating the first and second webs of fabric to thereby provide a laminated web of fabric therefrom.

This method can also advantageously have the dancingly controlling step including providing at least one dancer assembly positioned to receive one of the first and second webs of fabric for dancingly controlling tension in the respective one of the first and second webs of fabric and weightingly controlling the tension applied from the at least one dancer assembly to the web of fabric positioned thereon. The step of weightingly controlling the tension preferably includes adjustably increasing the weight of at least one fabric guide engaging a portion of the web of fabric to thereby increase the tension applied to the web of fabric and adjustably decreasing the weight of at least one fabric guide engaging the web of fabric to thereby decrease the tension applied to the web of fabric.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 2 is a perspective view of a portion of a second embodiment of a laminating apparatus having a dancer and a pair of air shaft assemblies according to the present invention;

FIG. 3 is fragmentary perspective view of an air shaft assembly of a laminating apparatus according to an embodiment of the present invention;

FIG. 4 is a side elevational view of an air shaft of a laminating apparatus having a roll of fabric being mounted thereon according to an embodiment of the present invention;

FIG. 5 is a sectional view of an air shaft of a laminating apparatus having a roll of fabric being mounted thereon and taken along line 5—5 of FIG. 4 according to an embodiment of the present invention;

FIG. 6 is a side elevational view of an air shaft of a laminating apparatus having a roll of fabric mounted thereon for rotation according to an embodiment of the present invention;

FIG. 7 is a sectional view of an air shaft of a laminating apparatus having a roll of fabric mounted thereon and taken along line 7—7 of FIG. 6 according to an embodiment of the present invention;

FIG. 8 is a sectional view of an air shaft assembly of a laminating apparatus taken along line 8—8 of FIG. 3 and illustrating air or gaseous pressure within an air shaft thereof according to an embodiment of the present invention;

FIG. 9 is an enlarged side elevational view of an air shaft assembly of a laminating apparatus have portions thereof broken away for clarity according to an embodiment of the present invention;

FIG. 10 is a fragmentary perspective view of a tension yoke of a dancer assembly of a laminating apparatus according to a third embodiment of the present invention;

FIG. 11 is a front elevational view of a vertically oriented dancer assembly of a laminating apparatus according to a third embodiment of the present invention;

FIG. 12 is a fragmentary top plan view of a vertically oriented dancer assembly of a laminating apparatus according to a third embodiment of the present invention;

FIG. 13 is a fragmentary front elevational view of a horizontally oriented dancer assembly according to a fourth embodiment of the present invention;

FIG. 14 is a side elevational view of a vertically oriented dancer assembly being rotatably mounted according to a third embodiment of the present invention; and FIG. 15 is a front elevational view of a vertically oriented dancer assembly being rotatably all mounted according to a third embodiment of the present invention.

DETAILED DESCRIPTION OF PREFERRED EMBODIMENTS

Figure 1:
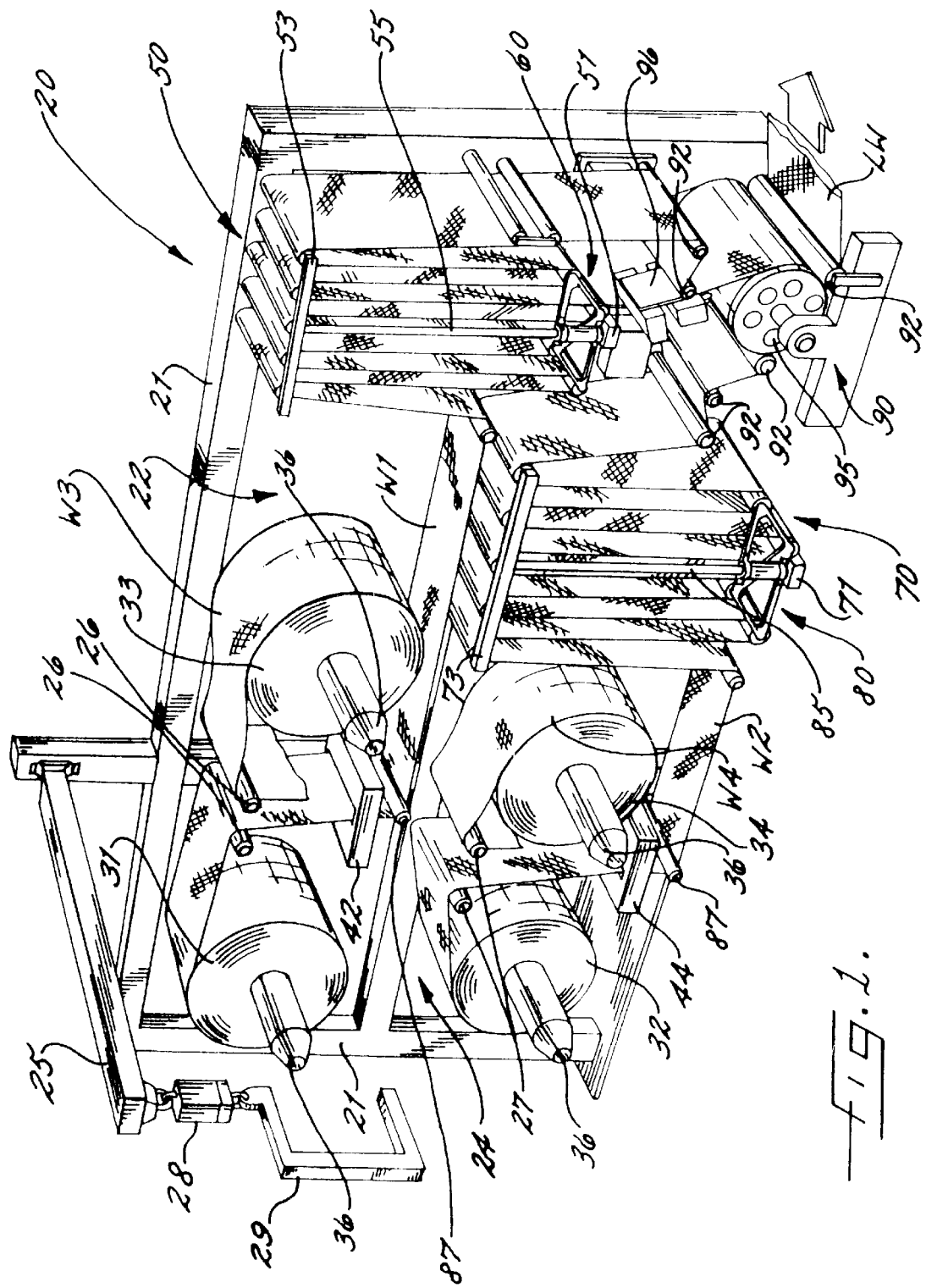
FIG. 1 is a perspective view of a first embodiment of a laminating apparatus having a pair of dancers and a plurality of air shaft assemblies according to the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and single, double, and triple prime notation, where used, indicate similar elements in alternative embodiments.

FIG. 1 illustrates a laminating apparatus 20 for providing a laminated fabric or laminated web LW for a disposable garment such as a toddler brief, adult undergarment, or disposable diaper. The laminating apparatus 20 preferably includes a laminating frame 21 having upper 22 and lower 24 laminating frame regions. The frame 21, for example, can advantageously be mounted on a manufacturing floor or other generally horizontal support or floor support surface.

The laminating apparatus 20 also has a first roll 31 of fabric mounted to the upper laminating frame ail region 22 so as to provide a first web W1 of fabric when unwound from the first fabric roll 31. A second roll 32 of fabric is preferably mounted to the lower laminating frame region 24 and positioned adjacent the first fabric roll 31 so as to provide a second web W2 of fabric when unwound from the second fabric roll 32. A third redundant roll 33 of fabric also can advantageously be mounted to the upper laminating frame region 22 and positioned adjacent the first fabric roll 31 so as to provide a third web W3 of fabric when unwound from the third fabric roll 33. Likewise, a fourth redundant roll 34 of fabric advantageously can be mounted to the lower frame region 24 and positioned adjacent the second and third fabric rolls 32, 33 so as to provide a fourth web W4 of fabric when unwound from the fourth fabric roll 34.

The rolls 31, 32, 33, 34, and more particularly the first and third rolls 31, 33, can advantageously be mounted to the frame by the use of a lifting assembly which preferably includes a frame boom member 25 connected to and extending outwardly from the frame 21. A lift adjusting member 28 is preferably connected to the boom member 25 and cooperates with the boom member for adjusting and positioning the lift and placement of one of the rolls 31, 32, 33, 34. A roll engagement member 29 is preferably connected to the lift adjusting member 28 for engagement of one of the rolls 31, 32, 33, 34 when lifting a roll for mounting or dismounting from the frame 21.

As perhaps best illustrated in FIGS. 1–2, the laminating apparatus 20, 20' can additionally include a first splicer 42, as readily understood by those skilled in the art, mounted to the upper laminating frame region 22 for splicing the third web W3 of fabric to the first web W1 of fabric. A second splicer 44, 44' as readily understood by those skilled in the art, also is preferably mounted to the lower laminating frame region 24 for splicing the fourth web W4 of fabric to the second web W2 of fabric. For example, once the first or second rolls 31, 32 of fabric begin to diminish or come to an end thereof, the third and/or fourth fabric rolls 33, 34 can advantageously be spliced to the first and/or second fabric rolls 31, 32 so that little or no interruption or down time in the manufacturing process occurs. Accordingly, the first and/or second fabric rolls 31, 32 can then be replaced by the lifting assembly so that the first and/or second fabric rolls 31, 32 can then be respectively spliced to the third and fourth fabric rolls 33, 34. The fabric, for example, is preferably a non-woven material, but woven or other laminating materials can advantageously be used as well according to the present invention. The apparatus can also advantageously include a plurality of upper and lower auxiliary guide rolls 26, 27 connected to the frame for guiding the fabric downstream such as to a splicing assembly as illustrated and described further herein.

As illustrated in FIGS. 1–2 and 10–15, the laminating apparatus 20, 20', 20", 20''' also preferably includes fabric dance controlling means mounted to the laminating frame 21, positioned downstream from at least the first and second fabric rolls 31, 32, and preferably also downstream from the third and fourth fabric rolls 33, 34, and positioned to receive at least the first and second webs W1, W2 of fabric therefrom for dancingly controlling the tension of at least the first and second webs W1, W2 of fabric being received it from at least the first and second fabric rolls 31, 32 and being supplied to fabric laminating means, e.g., preferably provided by a fabric laminator 90 as understood by those skilled in the art. The fabric laminator 90 is also preferably mounted to the laminating frame 21, positioned downstream from the fabric dance controlling means, and positioned to receive at least the first and second webs W1, W2 of fabric for combiningly laminating at least the first and second webs W1, W2 of fabric, and also preferably the third and fourth webs W3, W4 of fabric, to thereby provide a laminated web LW of fabric therefrom. The fabric laminator 90 preferably includes at least one draw roll 95 for drawing the webs of fabric from the rolls, i.e., through the dancer assemblies 50, 70 (see FIG. 1). The fabric laminator 90 preferably also includes a plurality of guide rollers 92 positioned for guiding the webs to and from the draw roll 95 and an adhesive applicator 96 for applying adhesive to at least one of the webs of fabric, e.g., directly or indirectly, so that the combined webs are drawn from or fed from the laminator 90 further downstream for use in disposable garments.

The fabric dance controlling means is preferably provided by one or more, and more preferably by at least two, dancer assemblies 50, 70 each positioned to receive one of the first and second webs W1, W2 of fabric for dancingly controlling tension in the respective one of the first and second webs W1, W2 of fabric. Each dancer assembly 50, 70 preferably includes a dancer frame 51, 53, and 71, 72, 73, a plurality of spaced-apart fabric guides 74 connected to the dancer frame 72, 73 and positioned to receive a web of fabric thereon, and fabric tension controlling means connected to the dancer frame 71, 72, 73 for dancingly controlling the tension in the web of fabric during movement across the plurality of spaced-apart fabric guides 74. The fabric tension controlling means preferably includes a track 55, 85, e.g., preferably provided by a pair of spaced-apart, elongate rods, connected to the dancer frame 71, 72, 73 and a tension yoke 60, 80 mounted for slidably following the track 55, 85. The tension yoke 80 preferably has a plurality of spaced-apart fabric guides 82 positioned to receive the web of fabric and for slidably following the movement of the tension yoke 80 when following the track 85. The tension yoke 80' also preferably includes a yoke frame 81' to which the fabric guides, e.g., rollers 82', are mounted and a pair of track followers 83' connected to the yoke frame 81' and mounted to the track 85', e.g., for slidably moving along each of the pair of spaced-apart rods (see, e.g., FIG. 2).

The fabric tension controlling means can also advantageously include a weight tension control assembly connected to the tension yoke 80" for weightingly controlling the tension applied from the tension yoke 80" to the web of fabric positioned thereon. In one embodiment, the weight tension control assembly can advantageously include at least one pulley 88, a cable 89 connected to the tension yoke 80''' and engaging the at least one pulley 88, and a weight adjuster or mounting member 87' connected to the cable 89 so that when the weight is adjustedly increased, the tension provided to the web of fabric engaged by the tension yoke 80''' is increased and when the weight is adjustedly decreased, the tension provided a web of fabric engaged by the tension yoke 80''' is decreased (see, e.g., FIG. 13). In an alternative embodiment, the weight tension control assembly can advantageously be connected more directly to the tension yoke 80" by having the weight adjuster or mounting member 87 be connected directly to and be integrally formed with a yoke frame 81" thereof (see, e.g., FIG. 10).

The dancer frame 71", 72", 73" preferably includes a pair of spaced-apart dancer frame members 71", 73", or 71", 72". The pair of space-apart dancer frame members 71", 73", for example, can longitudinally extend generally parallel to each other (see, e.g., FIGS. 11–12) or can have one frame member 72" longitudinally extending in a first direction and a second one 71" longitudinally extending in a second direction (see, e.g., FIGS. 2 and 14). The track 85" is preferably connected to each of the pair of spaced-apart dancer frame members 71", 73", or 71", 72" and extends therebetween. The tension yoke 80" is preferably positioned to slidably follow the track 85" between the pair of spaced-apart dancer frame members 71", 73", or 71", 72".

Additionally, each of the plurality of spaced-apart fabric guides 74, 82 of the first and second sets includes at least one roller, and more particularly preferably a plurality of rollers 74, 82. The first set of a plurality of spaced-apart rollers 74 is connected to one of the parallel dancer frame members 73 and/or 72, and more preferably is fixedly connected in a non-moving position thereto. Accordingly, the plurality of rollers 82 of the tension yoke 80 preferably are fixedly mounted to the yoke frame 81, but slidably move with the movement of the tension yoke 80 along the track 85. Each of the at least two dancer assemblies 50, 70 further includes at least two spaced-apart rollers 78 positioned adjacent at least portions of the dancer frame 71, 72, 73. It will be understood by those skilled in the art that the second set of rollers 82 move with the movement of the tension yoke 80, but as also understood by those skilled in the art the first set of fabric guides or rollers 74 could move instead and the second set could be more stationarily mounted like the first set. Also, alternatively, all of or only portions of both sets of fabric guides could move as well according to the present invention.

The generally parallel pair of spaced-apart dancer frame members 71, 73, or 71, 72 are also positioned generally parallel to a generally horizontally extending floor support surface which supports a frame 21 to which the apparatus 20 is mounted. Alternatively, as best illustrated in FIG. 13, the generally parallel pair of spaced-apart frame members 71, 73, or 71, 72 can be positioned to longitudinally extend in a plane transverse a generally horizontally extending floor support surface which supports a frame 21 to which the apparatus 20 is mounted.

Because a conventional dancer system, for example, provides little dynamic response and the tension control is non-linear, the apparatus of the present invention even further lengthens the arm or moving unit which pivots as compared to the travel distance of the arm. By extending the arm past a fulcrum, a counter weight can be used to offset the mass of the dancer rolls. This can be set to provide low or zero pre-load in the static mode. Such a system can work well, for example, for controlling the foam used in diaper waistbands. The material feed rate is low and provides plenty of dynamic response. If desired, one or more potientiometers, as understood by those skilled in the art, can be used to provide feedback on the position of the dancer rolls to automate the control process. The potientiometers can also be in electrical communication with a controller, such as a microprocessor based control system as understood by those skilled in the art, so that enhanced control of the apparatus can be achieved.

As web velocities increase and the desired web tension decreases, in some types of conventional dancer systems for example, better control of the dancer system is desired. Because of the lack of dynamic response in the convention dancer systems, a conflict can arise between the desire for long arms which can provide better tangent zones or movement ranges. To increase the amount of stored material, the apparatus adds dancer rolls as illustrated. This also advantageously decreases the amount of the web tension, but increases the bearing drag and dancer mass. In turn, this leads to greater hysterisis and lower frequency response. The arc from the arm can cause the web roller angles to change and reduce linearity. The apparatus, however, addresses these problems by allowing the moving rolls to stay in a desired alignment such as illustrated. More importantly, however, the apparatus as illustrated preferably uses linear bearings as understood by those skilled in the art to increase web material storage, enhance web material stay at a desired angle, and provide multiple web paths to reduce web tension. The weight of the dancer rolls of the apparatus can advantageously be adjusted to provide the desired web tension. The frame members, as illustrated, also can advantageously be hollow, such as hollow shafts, to reduce dancer mass. This design, as illustrated, also advantageously provides offset rolls for strength as well.

Further, as perhaps best illustrated in FIGS. 2–9, a laminating apparatus 20 of the present invention preferably also includes a plurality of air shaft assemblies 35 connected to the laminating frame 21. Each of the plurality of air shaft assemblies 35 preferably includes a gear housing 37, at least one gear 47, 48 positioned in the gear housing 37, and an air shaft 36 rotatably mounted to the gear housing 37 and being positioned to mount one of the rolls 31, 32, 33, 34 of fabric thereon (see, e.g., FIG. 9). The rotatable air shaft 36 includes an elongate shaft rod body and a plurality of roll engagement members 41 slidably movable between a first retracted position when positioned substantially flush with the shaft rod body and a second extended position when positioned to extend outwardly from the shaft rod body and abuttingly contact an inner surface of a roll of fabric mounted thereon (see FIGS. 3–8). Also, each of the plurality of air shaft assemblies 35 also includes a motor 38 connected to the gear housing 37 for imparting rotary motion to the rotatable air shaft through the at least one gear, e.g., a worm-type gear 47 and a sprocket-type gear 48, positioned in the gear housing 37 and a gaseous supply, e.g., a compressed air supply 39, for supplying a gas to the air shaft through the air lines 40 during rotary movement of the shaft 36 to thereby enhance the engagement of the roll engagement members 41 with one of the rolls 31, 32, 33, 34 of fabric mounted thereon.

As illustrated in FIGS. 1–15, the present invention also advantageously provides methods of laminating fabric for a disposable garment. A method preferably includes mounting a first roll 31 of fabric to a frame 21 so as to provide a first web W1 of fabric when unwound from the first fabric roll 31, mounting a second roll 32 of fabric to the frame 21 and positioned adjacent the first fabric roll 31 so as to provide a second web W2 of fabric when unwound from the second fabric roll 32, dancingly controlling the tension of at least one of the first and second webs W1, W2 of fabric being received from at least one of the first and second fabric rolls 31, 32, and combiningly laminating the first and second webs W1, W2 of fabric to thereby provide a laminated web LW of fabric. The dancingly controlling step can advantageously include providing at least one dancer assembly 50, 70 positioned to receive one of the first and second webs W1, W2 of fabric for dancingly controlling tension in the respective one of the first and second webs W1, W2 of fabric.

The method can also have the at least one dancer assembly 50, 70 including a dancer frame 71, 72, 73, a first set of a plurality of spaced-apart fabric guides 74 connected to the dancer frame 71, 72, 73, a track 85 connected to the dancer frame 71, 72, 73, and a tension yoke 80 mounted to the track 85. The method can further include slidably moving the tension yoke 80 to follow the track 85.

The method can further include weightingly controlling the tension applied from the tension yoke 80 to the web of fabric positioned thereon. The step of weightingly controlling the tension preferably includes adjustably increasing the weight of the tension yoke 80 to thereby increase the tension applied is to the web of fabric. The step of weightingly controlling the tension can also include adjustably decreasing the weight of the tension yoke 80 to thereby increase the tension applied to the web of fabric.

The method can still further include mounting a third redundant roll 33 of fabric to the frame 21 and positioned adjacent the first fabric roll 31 so as to provide a third web W# of fabric when unwound from the third fabric roll 33, mounting a fourth redundant roll 34 of fabric to the frame 21 and positioned adjacent the second and third fabric rolls 32, 33 so as to provide a fourth web W4 of fabric when unwound from the fourth fabric roll 34, positioning a first splicer 42 on the frame 21 for splicing the third web W3 of fabric to the first web W1 of fabric, and positioning a second splicer 44 on the frame 21 for splicing the fourth web W4 of fabric to the second web W2 of fabric.

Another method of laminating fabric for a disposable garment according to the present invention preferably includes dancingly controlling the tension of at least one of first and second webs W1, W2 of fabric being received from at least one of respective first and second fabric rolls 31, 32 and combiningly laminating the first and second webs W1, W2 of fabric to thereby provide a laminated web LW of fabric therefrom.

This method can also advantageously have the dancingly controlling step including providing at least one dancer assembly 50, 70 positioned to receive one of the first and second webs W1, W2 of fabric for dancingly controlling tension in the respective one of the first and second webs W1, W2 of fabric and weightingly controlling the tension applied from the at least one dancer assembly 50, 70 to the web of fabric positioned thereon. The step of weightingly controlling the tension preferably includes adjustably increasing the weight of at least one fabric guide 82 engaging a portion of the web of fabric to thereby increase the tension applied to the web of fabric and adjustably decreasing the weight of at least one fabric guide 82 engaging the web of fabric to thereby decrease the tension applied to the web of fabric.

A method of controlling tension in a web of fabric is also provided according to the present invention. A method preferably includes providing at least one dancer assembly 50, 70 having first and second sets of a plurality of spaced-apart fabric guides 74, 82 positioned to receive a web of fabric thereon. The first set of fabric guides 74 is also preferably spaced-apart from the second set of fabric guides 82. The method further includes positioning a web of fabric on the first and second sets of a plurality of spaced-apart fabric guides 74, 82, moving the web of fabric across the first and second sets of a plurality of spaced-apart fabric guides 74, 82, and dancingly moving at least one set 82 of the first and second sets of a plurality of fabric guides 74, 82 during movement of the web of fabric across the first and second sets of a plurality of spaced-apart fabric guides 74, 82.

The method can also have the dancingly moving step including weightingly controlling the tension applied from the at least one dancer assembly 50, 70 to the web of fabric positioned thereon. The weightingly controlling of the tension can be provided by adjustably increasing the weight of at least one of the plurality of fabric guides 82 of the first and second is sets of a plurality of fabric guides 74, 82 which dancingly move to thereby increase the tension applied to the web of fabric. The weightingly controlling the tension step can also advantageously include adjustably decreasing the weight of at least one of the plurality of fabric guides 82 of the first and second sets of a plurality of fabric guides 74, 82 which dancingly move to thereby decrease the tension applied to the web of fabric.

Other aspects of the dancer assemblies 50, 70 can also be seen in co-pending U.S. patent application Ser. No. 09/089,775 by the same inventors filed on Jun. 3, 1998 and which is incorporated herein by reference in its entirety.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

What is claimed is:

1. A laminating apparatus for providing a laminated fabric for a disposable garment, the apparatus comprising:
   a laminating frame having upper and lower laminating frame regions;
   a first roll of fabric mounted to the upper laminating frame region so as to provide a first web of fabric when unwound from said first fabric roll;
   a second roll of fabric mounted to the lower laminating frame region and positioned adjacent said first fabric roll so a to provide a second web of fabric when unwound from said second fabric roll;
   a third redundant roll of fabric mounted to the upper laminating frame region and positioned adjacent said first fabric roll so as to provide a third web of fabric when unwound from said third fabric roll;
   a fourth redundant roll of fabric mounted to the lower frame region and positioned adjacent said second and third fabric roll so as to provide a fourth web of fabric when unwound from said fourth fabric roll;
   a first splicer mounted to the upper laminating frame region for splicing the third web of fabric to the first web of fabric when said first web of fabric is near its end to thereby provide substantially continuous operation of the laminating apparatus;
   a second splicer mounted to the lower laminating frame region for splicing the fourth web of fabric to the second web of fabric when said second web of fabric is near its end to thereby provide substantially continuous operation of the laminating apparatus;
   fabric dance controlling means mounted to the laminating frame, positioned downstream from at least the first and second fabric rolls, and positioned to receive at least the first and second webs of fabric therefrom for independently and dancingly controlling the tension of at least the first and second webs of fabric being received from at least the first and second fabric rolls when maintaining constant speeds of the first and second fabric rolls by independently adjusting tension of the first and second fabric rolls to maintain a uniform tension on each of the first and second webs of fabric, the fabric dance controlling means comprising first and second dancer assemblies positioned downstream from the first and second fabric rolls to receive the respective first and second webs of fabric to dancingly control the tension of the respective first and second webs of fabric, the first and second dancer assemblies comprising fabric tension controlling means for weightingly adjusting the tension of the first and second webs of fabric by applying a preselected tension to the first and second webs of fabric defined by first and second preselected tensions independently applied to the respective first and second webs of fabric so that the preselected tension applied to the first web of fabric is independently adjusted from the preselected tension applied to the second web of fabric;
   fabric laminating means mounted to the laminating frame, positioned downstream from said fabric dance controlling means, and positioned to receive at least the first and second independently tensioned webs of fabric for combiningly laminating at least the first and second webs of fabric to thereby provide a uniformly laminated web of fabric therefrom; and
   a lifting assembly including a frame boom member connected to and extending outwardly from the laminating frame to lift at least the first and second fabric rolls to a preselected elevation to be mounted to the laminating frame, a lift adjusting member positioned in cooperation with the frame boom member for adjusting and positioning the placement of at least the first and second fabric rolls, and a roll engagement member connected to the lift adjusting member for engagement of at least the first and second fabric rolls to be mounted to the laminating frame.

2. An apparatus as defined in claim 1, wherein each of the first and second dancer assemblies includes a dancer frame, a first set of a plurality of spaced-apart fabric guides connected to the dancer frame, a track connected to the dancer frame, and a tension yoke mounted for slidably following said track, said tension yoke including a second set of a plurality of spaced-apart fabric guides positioned for slidably following the movement of said tension yoke when following said track.

3. An apparatus as defined in claim 2, wherein the dancer frame of each of the first and second dancer assemblies includes a pair of space-apart dancer frame members, said pair of space-apart dancer frame members longitudinally extending generally parallel to each other, said track being connected to each of said pair of spaced-apart dancer frame members and extending therebetween, said tension yoke being positioned to slidably follow said track between said generally parallel pair of spaced-apart dancer frame members.

4. An apparatus as defined in claim 3, wherein said laminating frame is mounted on a generally horizontally extending surface, and wherein said generally parallel pair of spaced-apart dancer frame members are also positioned generally parallel to the generally horizontally extending surface and further comprising a pivoting assembly connected to the laminating frame to rotate the dancer frame about a pivot point along a predetermined plane of rotation to thereby adjust the tension applied to the respective first and second webs of fabric positioned on the tension yoke.

5. An apparatus as defined in claim 3, wherein said laminating frame is mounted on a generally horizontally extending surface, and wherein each of said generally parallel pair of spaced-apart frame members is positioned to longitudially extend in a plane transverse the generally horizontally horizontally extending surface.

6. An apparatus as defined in claim 3, wherein each of said plurality of spaced-apart fabric guides of said first and second sets includes at least one roller, said first set of a plurality of spaced-apart rollers being connected to only one of said generally parallel pair of spaced-apart dancer frame members, wherein each of said at least two dancer assemblies further includes at least two spaced-apart rollers mounted to the laminating frame, wherein the tension yoke further comprises a counter weight positioned to offset the mass of the plurality of fabric guides, and wherein the dancer frame members are hollow to thereby reduce the mass of the dancer frame and reduce tension on at least the first and second webs of fabric.

7. A laminating apparatus for providing a laminated fabric for a disposable garment, the apparatus comprising:

a laminating frame having upper and lower laminating frame regions;

a first roll of fabric mounted to the upper laminating frame region so as to provide a first web of fabric when unwound from said first fabric roll;

a second roll of fabric mounted to the lower laminating frame region and positioned adjacent said first fabric roll so as to provide a second web of fabric when unwound from said second fabric roll;

a third redundant roll of fabric mounted to the upper laminating frame region and positioned adjacent said first fabric roll so as to provide a third web of fabric when unwound from said third fabric roll;

a fourth redundant roll of fabric mounted to the lower frame region and positioned adjacent said second and third fabric rolls so as to provide a fourth web of fabric when unwound from said fourth fabric roll;

a first splicer mounted to the upper laminating frame region for splicing the third web of fabric to the first web of fabric when said first web of fabric is near its end to thereby provide substantially continuous operation of the laminating apparatus;

a second splicer mounted to the lower laminating frame region for splicing the fourth web of fabric to the second web of fabric when said second web of fabric is near its end to thereby provide substantially continuous operation of the laminating apparatus;

fabric dance controlling means mounted to the laminating frame positioned downstream from at least the first and second fabric rolls, and positioned to receive at least the first and second webs of fabric therefrom for independently and dancingly controlling the tension of at least the first and second webs of fabric being received from at least the first and second fabric rolls when maintaining constant speeds of the first and second fabric rolls by independently adusting tension of the first and second fabric rolls to maintain a uniform tension on each of the first and second webs of fabric, the fabric dance controlling means comprising first and second dancer assemblies positioned downstream from the first and second fabric rolls to receive the respective first and second webs of fabric to dancingly controll the tension of the respective first and second webs of fabric, the first and second dancer assemblies comprising fabric tension controlling means for weightingly adjusting the tension of the first and second webs of fabric by applying a preselected tension to the first and second webs of fabric defined by first and second preselected tensions independently applied to the respective first and second webs of fabric so that the preselected tension applied to the first web of fabric is independently adjusted from the preselected tension applied to the second web of fabric, the first and second dancer assemblies further include a dancer frame, a first set of a plurality of spaced-apart fabric guides connected to the dancer frame, a rack connected to the dancer frame, and a tension yoke mounted for slidably following said track, said tension yoke including a second set of a plurality of spaced-apart fabric guides positioned for slidably following the movement of said tension yoke when following said track and wherein the fabric tension controlling means of each of the first and second dancer assemblies further includes a weight tension controll assembly connected to said tension yoke for independently and weightingly controlling the tension applied from said tension yoke to the respective first and second webs of fabric positioned thereon to thereby apply an independent and constant tension to each of the respective first and second webs of fabric;

fabric laminating means mounted to the laminating frame, positioned downstream from said fabric dance controlling means, and positioned to receive at least the first and second independently tensioned webs of fabric for combiningly laminating at least the first and second webs of fabric to thereby provide a uniformly laminated web of fabric therefrom; and a lifting assembly including a frame boom member connected to and extending outwardly from the laminating frame to lift at least the first and second fabric rolls to a preselected elevation to be mounted to the laminating frame, a lift adjusting member positioned in cooperation with the frame boom member for adjusting and positioning the placement of at least the first and second fabric rolls, and a roll engagement member connected to the lift adjusting member for engagement of at least the first and second fabric rolls to be mounted to the laminating frame.

8. An apparatus as defined in claim 7, wherein the dancer frame of each of the first and second dancer assemblies includes a pair of spaced-apart dancer frame members, said pair of spaced-apart dancer frame members longitudinally extending generally parallel to each other, said track being connected to each of said pair of spaced-apart dancer frame members and extending therebetween, said tension yoke being positioned to slidably follow said track between said generally parallel pair of spaced-apart dancer frame members.

9. An apparatus as defined in claim 8, wherein said laminating frame is mounted on a generally horizontally extending surface and wherein said generally parallel pair of spaced-apart dancer frame members are also positioned generally parallel to the generally horizontally extending surface and further comprising a pivoting assembly connected to the laminating frame to rotate the dancer frame about a pivot point along a predetermined plane of rotation to thereby adjust the tension applied to the respective first and second webs of fabric positioned on the tension yoke.

10. An apparatus as defined in claim 9, wherein said laminating frame is mounted on a generally horizontally extending surface, and wherein each of said generally parallel pair of spaced-apart frame members is positioned to longitudinally extend in a plane transverse the generally horizontally extending surface.

11. An apparatus as defined in claim 10, wherein each of said plurality of spaced-apart fabric guides of said first and second sets includes at least one roller, said first set of a plurality of spaced-apart rollers being connected to only one of said generally parallel pair of spaced-apart dancer frame members, wherein each of said at least two dancer assemblies further includes at least two spaced-apart rollers mounted to the laminating frame, wherein the tension yoke further comprises a counter weight positioned to offset the mass of the plurality of fabric guides, and wherein the dancer frame members are hollow to thereby reduce the mass of the dancer frame and educe tension on at least the first and second webs of fabric.

12. An apparatus as defined in claim 11, wherein said weight tension controll assembly includes at least one pulley, a cable connected to said tension yoke and engaging said at least one pulley, and a weight adjuster connected to said cable so that when the weight is adjustedly increased, the tension provided to the web of fabric engaged by said tension yoke is increased and when the weight is adjustedly decreased, the tension provided the web of fabric engaged by said tension yoke is decreased.

13. An apparatus as defined in claim 7, wherein said weight tension control assembly includes at least one pulley, a cable connected to said tension yoke and engaging said at least one pulley, and a weight adjuster connected to said cable so that when the weight is adjustedly increased, the tension provided to the web of fabric engaged by said tension yoke is increased and when the weight is adjustedly decreased, the tension provided the web of fabric engaged by said tension yoke is decreased.

14. An apparatus as defined in claim 7, further comprising a plurality of air shaft assemblies connected to said laminating frame, each of said plurality of air shaft assemblies including a gear housing, at least one gear positioned in said gear housing, and a rotatable air shaft mounted to said gear housing and being positioned to mount one of the rolls of fabric thereon, the rotatable air shaft including an elongate shaft rod body and a plurality of roll engagement members slidably movable between a first retracted position when positioned substantially flush with said shaft rod body and a second extended position when positioned to extend outwardly from said shaft rod body and abuttingly contact an inner surface of a roll of fabric mounted thereon, the plurality of roll engagement members being configured in a row of roll engagement members positioned along outer peripheries of the shaft rod body, wherein the row of roll engagement members includes more than three roll engagement members, and wherein the air shaft assembly comprises a plurality of rows of roll engagement members.

15. A laminating apparatus for providing a laminated fabric for a disposable garment, the apparatus comprising:

a laminating frame having upper and lower laminating frame regions;

a first roll of fabric mounted to the upper laminating frame region so as to provide a first web of fabric when unwound from said first fabric roll;

a second roll of fabric mounted to the lower laminating frame region and positioned adjacent said first fabric roll so as to provide a second web of fabric when unwound from said second fabric roll;

a third redundant roll of fabric mounted to the upper laminating frame region and positioned adjacent said first fabric roll so as to provide a third web of fabric when unwound from said third fabric roll;

a fourth redundant roll of fabric mounted to the lower frame region and positioned adjacent said second and third fabric rolls so as to provide a fourth web of fabric when unwound from said fourth fabric roll;

a first splicer mounted to the upper laminating frame region for splicing the third web of fabric to the first web of fabric when said first web of fabric is near its end to thereby provide substantially continuous operation of the laminating apparatus;

a second splicer mounted to the lower laminating frame region for splicing the fourth web of fabric to the second web of fabric when said second web of fabric is near its end to thereby provide substantially continuous operation of the laminating apparatus;

fabric dance controlling means mounted to the laminating frame positioned downstream from at least the first and second fabric rolls, and positioned to receive at least the first and second webs of fabric therefrom for independently and dancingly controlling the tension of at least the first and second webs of fabric being received from at least the first and second fabric rolls when maintaining constant speeds of the first and second fabric rolls by independently adjusting tension of the first and second fabric rolls to maintain a uniform tension on each of the first and second webs of fabric, the fabric dance controlling means comprising first and second dancer assemblies positioned downstream from the first and second fabric rolls to receive the respective first and second webs of fabric to dancingly controll the tension of the respective first and second webs of fabric, the first and second dancer assemblies comprising fabric tension controlling means for weightingly adjusting the tension of the first and second webs of fabric by applying a preselected tension to the first and second webs of fabric defined by first and second preselected tensions independently applied to the respective first and second webs of fabric so that the preselected tension applied to the first web of fabric is independently adjusted from the preselected tension applied to the second web of fabric;

fabric laminating means mounted to the laminating frame, positioned downstream from said fabric dance controlling means, and positioned to receive at least the first and second independently tensioned webs of fabric for combiningly laminating at least the first and second webs of fabric to thereby provide a uniformly laminated web of fabric therefrom;

a lifting assembly including a frame boom member connected to and extending outwardly from the laminating frame to lift at least the first and second fabric rolls to a preselected elevation to be mounted to the laminating frame, a lift adjusting member positioned in cooperation with the frame boom member for adjusting and positioning the placement of at least the first and second fabric rolls, and a roll engagement member connected to the lift adjusting member for engagement of at least the first and second fabric rolls to be mounted to the laminating frame; and a plurality of air shaft assemblies connected to said laminating frame, each of said plurality of air shaft assemblies including a gear housing, at least one gear positioned in said gear housing, and a rotatable air shaft mounted to said gear housing and being positioned to mount one of the rolls of fabric thereon, the rotatable air shaft including an elongate shaft rod body and a plurality of roll engagement members slidably movable between a first retracted position when positioned substantially flush with said shaft rod body and a second extended position when positioned to extend outwardly from said shaft rod body and abuttingly contact an inner surface of a roll of fabric mounted thereon, the plurality of roll engagement members being configured in a row of roll engagement members positioned along outer peripheries of the shaft rod body, wherein the row of roll engagement members includes more than three roll engagement members, and wherein the air shaft assembly comprises a plurality of rows of roll engagement members.

16. An apparatus as defined in claim 15, wherein each of the first and second dancer assemblies includes a dancer frame, a first set of a plurality of spaced-apart fabric guides connected to the dancer frame, a track connected to the dancer frame, and a tension yoke mounted for slidably following said track, said tension yoke including a second set of a plurality of spaced-apart fabric guides positioned for slidably following the movement of said tension yoke when following said track.

17. An apparatus as defined in claim 16, wherein the dancer frame of each of the first and second dancer assemblies includes a pair of space-apart dancer frame members, said pair of space-apart dancer frame members longitudinally extending generally parallel to each other, said track being connected to each of said pair of spaced-apart dancer frame members and extending therebetween, said tension yoke being positioned to slidably follow said track between said generally parallel pair of spaced-apart dancer frame members.

18. An apparatus as defined in claim 17, wherein said laminating frame is mounted on a generally horizontally extending surface, and wherein said generally parallel pair of spaced-apart dancer frame members are also positioned generally parallel to the generally horizontally extending surface and further comprising a pivoting assembly connected to the laminating frame to rotate the dancer frame about a pivot point also a predetermined plane of rotation to thereby adjust the tension applied to the respective first and second webs of fabric positioned on the tension yoke.

19. An apparatus as defined in claim 18, wherein said laminating frame is mounted on a generally horizontally extending surface, and wherein each of said generally parallel pair of spaced-apart frame members is positioned to longitudinally extend in a plane transverse the generally horizontally extending surface.

20. An apparatus as defined in claim 19, wherein each of said plurality of spaced-apart fabric guides of said first and second sets includes at least one roller, said first set of a plurality of spaced-apart rollers being connected to only one of said generally parallel pair of spaced-apart dancer frame members, wherein each of said at least two dancer assemblies further includes at least two spaced-apart rollers mounted to the laminating frame, wherein the tension yoke further comprises a counter weight positioned to offset the mass of the plurality of fabric guides, and wherein the dancer frame members are hollow to thereby reduce the mass of the dancer frame and reduce tension on at least the first and second webs of fabric.

21. An apparatus as defined in claim 20, wherein the fabric tension controlling means of each of the first and second dancer assemblies further includes a weight tension controll assembly connected to said tension yoke for independently and weightingly controlling the tension applied from said tension yoke to the respective first and second webs of fabric positioned thereon to thereby apply an independent and constant tension to each of the respective first and second webs of fabric.

22. An apparatus as defined in claim 21, wherein said weight tension controll assembly includes at least one pulley, a cable connected to said tension yoke and engaging said at least on pulley, and a weight adjuster connected to said cable so that when the weight is adjustedly increased, the tension provided to the web of fabric engaged by said tension yoke is increased and when the weight is adjustedly decreased, the tension provided the web of fabric engaged by said tension yoke is decreased.

\* \* \* \* \*